(12) United States Patent
Poewe (10) Patent No.: US 8,809,310 B2
(45) Date of Patent: Aug. 19, 2014

(54) USE OF RASAGILINE FOR THE TREATMENT OF MULTIPLE SYSTEM ATROPHY

(75) Inventor: Werner Poewe, Innsbruck (AT)

(73) Assignee: Teva Pharmaceutical Industries, Ltd., Petach-Tikva (IL)

( * ) Notice: Subject to any disclaimer, the term of this patent is extended or adjusted under 35 U.S.C. 154(b) by 694 days.

(21) Appl. No.: 12/223,794

(22) PCT Filed: Feb. 21, 2007

(86) PCT No.: PCT/US2007/004884
§ 371 (c)(1),
(2), (4) Date: Oct. 3, 2008

(87) PCT Pub. No.: WO2007/098264
PCT Pub. Date: Aug. 30, 2007

(65) Prior Publication Data
US 2010/0168239 A1    Jul. 1, 2010

Related U.S. Application Data

(60) Provisional application No. 60/874,341, filed on Dec. 12, 2006, provisional application No. 60/775,147, filed on Feb. 21, 2006.

(51) Int. Cl.
*A01N 43/00* (2006.01)
*A01N 37/12* (2006.01)

(52) U.S. Cl.
USPC ............................... 514/183; 514/567

(58) Field of Classification Search
None
See application file for complete search history.

(56) References Cited

U.S. PATENT DOCUMENTS

| | | | |
|---|---|---|---|
| 5,387,612 A | 2/1995 | Youdim et al. | |
| 5,453,446 A | 9/1995 | Youdim et al. | |
| 5,457,133 A | 10/1995 | Youdim et al. | |
| 5,486,541 A | 1/1996 | Sterling et al. | |
| 5,519,061 A | 5/1996 | Youdim et al. | |
| 5,532,415 A | 7/1996 | Youdim et al. | |
| 5,576,353 A | 11/1996 | Youdim et al. | |
| 5,599,991 A | 2/1997 | Youdim et al. | |
| 5,668,181 A | 9/1997 | Youdim et al. | |
| 5,744,500 A | 4/1998 | Youdim et al. | |
| 5,786,390 A | 7/1998 | Youdim et al. | |
| 5,891,923 A * | 4/1999 | Youdim et al. ............. | 514/657 |
| 6,126,968 A | 10/2000 | Peskin et al. | |
| 6,277,886 B1 | 8/2001 | Levy et al. | |
| 6,316,504 B1 | 11/2001 | Youdim et al. | |
| 6,462,222 B1 | 10/2002 | Chorev et al. | |
| 6,630,514 B2 | 10/2003 | Youdim et al. | |
| 6,635,667 B2 | 10/2003 | Thomas | |
| 6,929,801 B2 * | 8/2005 | Klose et al. ............. | 424/448 |
| 6,956,060 B2 | 10/2005 | Youdim et al. | |
| 7,396,860 B2 | 7/2008 | Blaugrund et al. | |
| 7,491,847 B2 | 2/2009 | Frenkel | |
| 7,547,806 B2 | 6/2009 | Frenkel et al. | |
| 7,572,834 B1 | 8/2009 | Sterling et al. | |
| 7,598,420 B1 | 10/2009 | Sterling et al. | |
| 7,619,117 B1 | 11/2009 | Lidor-Hadas et al. | |
| 7,750,051 B2 | 7/2010 | Frenkel et al. | |
| 7,815,942 B2 | 10/2010 | Peskin | |
| 7,855,233 B2 | 12/2010 | Frenkel et al. | |
| 7,968,749 B2 | 6/2011 | Frenkel et al. | |
| 8,080,584 B2 | 12/2011 | Safadi et al. | |
| 8,143,315 B2 | 3/2012 | Stahl | |
| 8,334,409 B2 | 12/2012 | Frenkel | |
| 2004/0176469 A1 * | 9/2004 | Thomas ................. | 514/649 |
| 2006/0018957 A1 | 1/2006 | Lerner et al. | |
| 2006/0094783 A1 | 5/2006 | Youdim et al. | |
| 2006/0188581 A1 | 8/2006 | Peskin | |
| 2007/0100001 A1 | 5/2007 | Youdim et al. | |
| 2007/0112217 A1 | 5/2007 | Frenkel et al. | |
| 2007/0232700 A1 | 10/2007 | Blaugrund et al. | |
| 2008/0146676 A1 | 6/2008 | Frenkel et al. | |
| 2008/0161408 A1 | 7/2008 | Frenkel et al. | |
| 2009/0062400 A1 | 3/2009 | Oron et al. | |
| 2009/0076160 A1 | 3/2009 | Lendvai et al. | |
| 2009/0111892 A1 | 4/2009 | Patashnik et al. | |
| 2009/0181086 A1 | 7/2009 | Safadi et al. | |
| 2009/0312436 A1 | 12/2009 | Levy et al. | |
| 2009/0318564 A1 | 12/2009 | Frenkel et al. | |
| 2010/0008983 A1 | 1/2010 | Safadi et al. | |
| 2010/0010095 A1 | 1/2010 | Frenkel | |
| 2010/0010098 A1 | 1/2010 | Elffrink | |
| 2010/0029987 A1 | 2/2010 | Allegrini et al. | |

(Continued)

FOREIGN PATENT DOCUMENTS

| | | |
|---|---|---|
| CA | 2174449 | 4/1995 |
| WO | WO 95/11016 | 4/1995 |

(Continued)

OTHER PUBLICATIONS

Souza et al. ("Dityrosine Cross-Linking Promotes Formation of Stable a-Synuclein Polymers", J Biol Chem., 275(24) 2000:18344-18349).*
(Klutin et al. "Chartacteristics of the Dysarthria of Multiple System atrophy"; Arch Neurol/vol. 53, Jun. 1996, pp. 545-548).*
Colosimo et al., (J. Neural. Transm., 2005, 112(12), pp. 1695-1704).*
International Preliminary Report on Patentability and the Written Opinion of the International Searching Authority for International Application No. PCT/US07/04884, issued Oct. 14, 2008.
U.S. Appl. No. 11/791,684, filed May 24, 2007, Patashnik et al.
U.S. Appl. No. 12/283,946, filed Sep. 16, 2008, Lendvai et al.
U.S. Appl. No. 12/231,601, filed Sep. 3, 2008, Oron et al.

(Continued)

*Primary Examiner* — Snigdha Maewall
(74) *Attorney, Agent, or Firm* — John P. White; Gary J. Gershik; Cooper & Dunham LLP (57) ABSTRACT

Disclosed is a method for the treatment of Multiple System Atrophy comprising administering to a subject an amount of R(+)-N-propargyl-1-aminoindan or a pharmaceutically acceptable salt thereof.

18 Claims, 6 Drawing Sheets

(56) References Cited

U.S. PATENT DOCUMENTS

| | | |
|---|---|---|
| 2010/0137447 A1 | 6/2010 | Lehmann et al. |
| 2010/0144887 A1 | 6/2010 | Frenkel et al. |
| 2010/0145101 A1 | 6/2010 | Frenkel et al. |
| 2010/0189787 A1 | 7/2010 | Safadi et al. |
| 2010/0189788 A1 | 7/2010 | Safadi et al. |
| 2010/0189790 A1 | 7/2010 | Safadi et al. |
| 2010/0189791 A1 | 7/2010 | Safadi et al. |
| 2010/0190859 A1 | 7/2010 | Frenkel et al. |
| 2010/0234636 A1 | 9/2010 | Stahl |
| 2011/0130466 A1 | 6/2011 | Lorenzl |
| 2011/0152381 A1 | 6/2011 | Frenkel et al. |
| 2011/0313050 A1 | 12/2011 | Rimkus et al. |
| 2012/0003310 A1 | 1/2012 | Safadi et al. |
| 2012/0029087 A1 | 2/2012 | Petit et al. |
| 2012/0059058 A1 | 3/2012 | Lorimer et al. |
| 2012/0100189 A1 | 4/2012 | Safadi et al. |
| 2012/0101168 A1 | 4/2012 | Bahar et al. |
| 2012/0238636 A1 | 9/2012 | Patashnik et al. |
| 2012/0263789 A1 | 10/2012 | Safadi et al. |
| 2013/0089610 A1 | 4/2013 | Safadi et al. |
| 2013/0089611 A1 | 4/2013 | Ulanenko et al. |
| 2013/0089612 A1 | 4/2013 | Safadi et al. |

FOREIGN PATENT DOCUMENTS

| | | | |
|---|---|---|---|
| WO | WO 01-32170 | | 5/2001 |
| WO | WO 01-78711 | | 10/2001 |
| WO | WO 2004-022128 | | 4/2004 |
| WO | WO2006062465 | * | 6/2006 |
| WO | 2007098264 | | 8/2007 |
| WO | WO 2008/019871 | | 2/2008 |
| WO | WO 2008/131961 | | 11/2008 |
| WO | WO 2009/081148 | | 7/2009 |
| WO | WO 2009/122301 | | 10/2009 |
| WO | WO 2009/152777 | | 12/2009 |
| WO | WO 2010/007181 | | 1/2010 |
| WO | WO 2010/013048 | | 2/2010 |
| WO | WO 2010/049379 | | 5/2010 |
| WO | WO 2010/070090 | | 6/2010 |
| WO | WO 2011/003938 | | 1/2011 |
| WO | WO 2011/009873 | | 1/2011 |
| WO | WO 2011/010324 | | 1/2011 |

OTHER PUBLICATIONS

U.S. Appl. No. 12/283,107, filed Sep. 8, 2008 (Sterling et al.) (including specification and pending claim set).

U.S. Appl. No. 12/901,281, filed Oct. 8, 2010 (Lorenzl) (including specification and pending claim set).

U.S. Appl. No. 12/974,769, filed Dec. 21, 2010 (Frenkel et al.) (including specification and pending claim set).

International Search Report for International Application No. PCT/US07/04884, issued Sep. 24, 2008.

U.S. Appl. No. 12/283,107, filed Sep. 8, 2008 (Sterling et al.).

U.S. Appl. No. 13/192,019, filed Jul. 27, 2011 (Petit et al.).

U.S. Appl. No. 13/281,054, filed Oct. 25, 2011 (Bahar et al.).

Schapira et al., Rasagiline in neurodegeneration, Experimental Neurology, Academic Press, vol. 212, No. 2, Aug. 1, 2008, pp. 255-257.

Stefanova et al., Rasagiline is neuroprotective in a transgenic model of multiple system atrophy, Experimental Neur., Academic Press, vol. 2010, No. 2, Dec. 4, 2007.

Tolosa, E., Early signs of PD—Can they be sued for diagnosis, European Journal of Neurology, vol. 13, No. Suppl. 2, Sep. 2006, pp. 6324-6325.

Feb. 16, 2012 Office Action issued in Australian Patent Application No. 2007217349.

Oct. 4, 2011 Supplemental Search Report issued in European Patent Application No. 07751629.2.

Apr. 30, 2012 Response to Supplemental Search Report issued in European Patent Application No. 07751629.2.

U.S. Appl. No. 13/651,307, Oct. 12, 2012, Levy et al.

U.S. Appl. No. 13/647,658, Oct. 9, 2012, Ulanenko et al.

U.S. Appl. No. 13/647,685, Oct. 9, 2012, Safadi et al.

U.S. Appl. No. 13/647,622, Oct. 9, 2012, Safadi et al.

Jul. 3, 2012 Office Action issued by the Japanese Patent Office in connection with Japanese Patent Application No. 208-556464, filed Aug. 21, 2008 with English translation.

Nov. 2, 2012 Response to Jul. 3, 2012 Office Action issued by the Japanese Patent Office in connection with Japanese Patent Application. No. 2008-556464, filed Aug. 21, 2008 with English draft sent to Foreign Associates for filing.

Dec. 11, 2012 Official Action issued by European Patent Office in connection with European Patent Application No. 07751629.2

Dec. 18, 2012 Decision of Rejection. issued by the Japanese Patent Office in connection with Japanese Patent Application No. 2008-556464, filed Aug. 21, 2008 with English translation.

Diagnosis and Treatment, 2004, vol. 92, No. 5, pp. 772-776 (no English translation available).

Flabeau at al., "Multiple system atrophy: current and future approaches to management" *Therapeutic Advances in Neurological Disorders* (2010), 3(4) 249-263.

Lipp et al., "Prospective Differentiation of Multiple System Atrophy from Parkinson Disease, Without Autonomic Failure", *Arch Neurol*, (2009), 66(6), p. 742 & p. 746.

Naoi, et al., "Oxidative Stress in Mitochondria: Decision to Survival and Death of Neurons in Neurodegenerative Disorders," Mol. Neurobiol., 2005, vol. 31, p. 81-93.

Stefanova et al., "Oxidative Stress in Transgenic Mice with Oligodendroglial α-Synuclein Overexpression Replicates the Characteristic Neuropathology of Multiple System Atrophy," Am. J. Pathol., 2005, vol. 166, p. 869-876.

U.S. Appl. No. 13/859,625, Apr. 9, 2013, Levy, et al.

Apr. 18, 2013 Appeal in response to Dec. 18, 2012 Decision of Rejection issued by the Japanese Patent Office in connection with Japanese Patent Application No. 2008-556464, filed Aug. 21, 2008.

Apr. 11, 2013 Response to Dec. 11, 2012 Official Action issued by European Patent Office in connection with European Patent Application. No. 07751629.2.

Feb. 13, 2013 Response to Feb. 16, 2012 Office Action issued in Australian Patent Application No. 2007217349.

Jan. 25, 2013 Official Action issued by the Canadian Patent Office in connection with Canadian Patent Application No. 2,643,235.

Jul. 25, 2013 Response to Jan. 25, 2013 Official Action issued by the Canadian Patent Office in connection with Canadian Patent Application No. 2,643,235.

Feb. 19, 2013 Official Action issued by the Australian Patent Office in connection with Australian Patent Application No. 2007217349.

Apr. 15, 2013 Response to Feb. 19, 2013 Official Action issued by the Australian Patent Office in connection with Australian Patent Application No. 2007217349.

U.S. Appl. No. 13/967,240, Aug. 14, 2013, Rimkus et al.

U.S. Appl. No. 13/969,295, Aug. 16, 2013, Fitzer-Attas et al.

U.S. Appl. No. 14/016,960, Sep. 3, 2013, Lehmann et al.

\* cited by examiner

USE OF RASAGILINE FOR THE TREATMENT OF MULTIPLE SYSTEM ATROPHY

This application is a §371 national stage of PCT International Application No. PCT/US2007/004884, filed Feb. 21, 2007, and claims the benefit of U.S. Provisional Applications Nos. 60/874,341, filed Dec. 12, 2006 and 60/775,147, filed Feb. 21, 2006, the contents of all of which are hereby incorporated by reference into this application.

Throughout this application various publications, published patent applications, and patents are referenced. The disclosures of these documents in their entireties are hereby incorporated by reference into this application in order to more fully describe the state of the art to which this invention pertains.

BACKGROUND OF THE INVENTION

Multiple System Atrophy (MSA) is a progressive neurodegenerative disease of undetermined cause that occurs sporadically and causes parkinsonism, cerebellar, pyramidal autonomic and urological dysfunction in any combination (Kaufman, H., Multiple System Atrophy, Neurology 1998, 11:351-55, citing The Consensus Committee of the American Autonomic Society and the American Academy of Neurology, Consensus statement on the definition of orthostatic hypotension, pure autonomic failure, and multiple system atrophy, Neurology 1996, 46:1470; Wenning et al., Multiple System Atrophy, Lancet Neurol. 2004, 3(2):93-103). The disease has historically been subcategorized by its predominant form of expression: striatonigral degeneration (SND) for parkinsonism, Shy-Drager syndrome (SDS) for autonomic failure, and sporadic olivopontocerebellar atrophy (OPCA) for cerebellar features.

However, glial cytoplasmic inclusions (GCI) in the brain of patients with MSA provide a pathological marker for the disorder (akin to Lewy bodies in Parkinson's disease), which confirms that SND, SDS and OPCA are the same disease with different clinical expression. (Kaufmann, supra, citing Lantos, P. L., Multiple System Atrophy, Brain Pathology 1997, 7:1293-97).

In addition, although MSA is often misdiagnosed as Parkinson's disease (PD), MSA is a separate and distinct disorder from PD. Both diseases cause stiffness and slowness in early stages, but the additional symptoms of MSA, such as dizziness and difficulty swallowing, are unusual in early PD. (Sarah Matheson Trust for MSA, at http://www.msaweb.co.uk/faq.htm).

Moreover, life expectancy in MSA is known to be shorter than in Parkinson's disease. An analysis of published case reports over a 100 year period showed that mean age of onset was 54 years (range 31-78) and survival 6 years (range 0.5-24). Survival was unaffected by gender, parkinsonian or pyramidal features, or whether the patient was classified as SND or OPCA (Ben-Schlomo et al. 1997).

As patients with MSA often present a predominantly parkinsonian form of the disorder (the striatonigral variety) or a largely cerebellar form (the OPCA-variety) new terms such as MSA-P and MSA-C have been proposed. (Gillman et al. 1999) Although most patients demonstrate one of these two forms, many have overlapping features, often with pyramidal tract deficit in addition to dysautonomic features (Mitra et al. 2003).

The most common symptoms of MSA-P include tremor, muscular rigidity and hypokinesia (decreased mobility, motor function or activity).

The most common symptoms of MSA-C include ataxia (failure of muscular coordination), impaired balance, impaired speech and impaired swallowing. (National Dysautonomia Research Foundation, at http://www.ndrf.org/MSA.htm). When the main presenting symptom is cerebellar, MSA may be confused with other cerebellar ataxias (Kaufmann 1998).

SDS or autonomic failure symptoms include: orthostatic hypotension, which includes lightheadedness, tiredness, blurred vision and pain in the rear of the neck; impotence, urinary incontinence or retention. Autonomic failure is present in 97% of cases (Rehman 2001). When the sole initial deficit is autonomic (i.e., orthostatic hypotension, erectile dysfunction), MSA mimics pure autonomic failure or an autonomic neuropathy.

There is no specific treatment for the various features of MSA and therefore medical treatment tends to be aimed at mitigating the parkinsonian and autonomic features of the disease (Colosimo et al 2002). Poor or no therapeutic response to levodopa is a well known characteristic of MSA-P. Dopamine agonists such as bromocriptine (Goetz et al 1984), lisuride (Lees et al 1981) and apomorphine (Rossi et al 2000) and glutamine antagonists such as amantadine have been tested with mixed results. Attempts to treat the autonomic dysfunction have focused on orthostatic hypotension therapies such as fludrocortisone and midodrine. Anticholinergics have been shown to help with the various urinary symptoms of the condition.

At present there is no recognized therapy for either treating MSA itself or its various features, leading at least one author to described the various therapeutic options currently available as 'dismal' (Kaufmann 1998).

Rasagiline, R(+)-N-propargyl-1-aminoindan, is a potent second generation monoamine oxidase (MAO) B inhibitor (Finberg et al., Pharmacological properties of the anti-Parkinson drug rasagiline; modification of endogenous brain amines, reserpine reversal, serotonergic and dopaminergic behaviours, *Neuropharmacology* (2002) 43(7):1110-8). Rasagiline Mesylate in a 1 mg tablet is commercially available for the treatment of idiopathic Parkinson's disease as AZILECT® from Teva Pharmaceuticals Industries, Ltd. (Petach Tikva, Israel) and H. Lundbeck A/S (Copenhagen, Denmark). Recent studies have demonstrated that, in addition to its MAO-B inhibitor activity, rasagiline possesses potent neuroprotective activity demonstrated by in vitro and in vivo experiments. Neuroprotection by rasagiline was achieved in animal models of closed head trauma (Huang et al., Neuroprotective effect of rasagiline, a selective monoamine oxidase-B inhibitor, against closed head injury in the mouse, Eur. J. Pharmacol. (1999) 366(2-3):127-35), global focal ischemia (Speiser et al., Studies with rasagiline, a MAO-B inhibitor, in experimental focal ischemia in the rat, *J. Neural Transm.* (1999) 106(7-8):695-606) and MPTP-induced neurotoxicity (Sage et al. 2001, 2003) as well as transgenic model of amyotrophic lateral sclerosis (Waibel et al., Rasagiline alone and in combination with riluzole prolongs survival in an ALS mouse model, *J. Neurol.* (2004) 251(9):1080-4) and 6-OHDA model of PD (Blandini et al., Neuroprotective effect of rasagiline in a rodent model of Parkinson's disease, *Exp. Neurol.* (2004) 187(2):455-9). Cell culture experiments have shown that rasagiline potently suppresses apoptotic cell death initiated by mitochondria (Youdim et al., Rasagiline [N-propargyl-1R-(+)-aminoindan], a selective and potent inhibitor of mitochondrial monoamine oxidase B *Br. J. Pharmacol.* (2001) 132(2):500-6; Akao et al., Mitochondrial permeability transition mediates apoptosis induced by N-methyl(R)salsolinol, an endogenous neurotoxin, and is inhibited by Bcl-2 and rasagiline, N-propargyl-1(R)-aminoindan, *J. Neurochem.* (2002) 82(4):913-23) by preventing preapoptotic swelling of mitochondria, caspase 3 activation, activation of nuclear PARP-1, translocation of GADPH, and nucleasomal DNA fragmentation (Youdim and Weinstock, Molecular basis of neuroprotective activities of rasagiline and the anti-Alzheimer drug TV3326 [(N-propargyl-(3R)aminoindan-5-YL)-ethyl methyl carbamate], *Cell Mol. Neurobiol.* (2001) 21(6): 555-73; Youdim et al., Amyloid processing and signal transduction properties of antiparkinso-antialzheimer neuroprotective drugs rasagiline and TV3326, *Ann. N.Y. Acad. Sci.* (2003) 993:378-86; Bar-am et al., Regulation of protein kinase C by the anti-Parkinson drug, MAO-B inhibitor, rasagiline and its derivatives, in vivo, *J. Neurochem.* (2004) 89(5): 1119-25; and Weinreb et al., Neuroprotectoin via pro-survival protein kinase C isoforms associated with Bcl-2 family members, *Faseb J.* (2004) 18(12):1471-3). Further, rasagiline induces increase of the anti-apoptotic Bcl-2 and Bcl-xL expression parallel to downregulation of pro-apoptotic Bad and Bax (Youdim et al., The essentiality of Bcl-2, PKC and proteasome-ubiquitin complex activations in the neuroprotective-antiapoptotic action of the anti-Parkinson drug, rasagiline, *Biochem. Pharmacol.* (2003) 66(8):1635-41; Yogev-Falach et al., The importance of propargylamine moiety in the anti-Parkinson drug rasagiline and its derivatives in MAPK-dependent amyloid precursor protein processing, *Faseb J.* (2003) 17(15):2325-7; Bar-Am et al., supra). Recent evidence from a delayed-start design study in PD has suggested potential disease-modifying efficacy of rasagiline also in a clinical setting (Parkinson Study, G., A controlled, randomized, delayed-start study of rasagiline in early Parkinson disease, *Arch. Neurol.* (2004) 61(4):561-6).

SUMMARY OF THE INVENTION

The subject invention provides a method of treating a subject suffering from Multiple System Atrophy, comprising administering to the subject an amount of R(+)-N-propargyl-1-aminoindan or a pharmaceutically acceptably salt thereof effective to treat the subject.

The subject invention also provides a method of alleviating a symptom of Multiple System Atrophy in a subject afflicted with Multiple System Atrophy, comprising administering to the subject an amount of R(+)-N-propargyl-1-aminoindan or a pharmaceutically acceptable salt thereof effective to alleviate the symptom of Multiple System Atrophy in the subject.

The subject invention also provides a pharmaceutical composition comprising in unit dosage form R(+)-N-propargyl-1-aminoindan or a pharmaceutically acceptable salt thereof and at least one of dopamine agonists, glutamine antagonists, orthostatic hypotension therapeutics, anticholinergics, or drugs to treat male impotence.

The subject invention also provides a pharmaceutical composition for use in the treatment of, or alleviation of symptoms of, Multiple System Atrophy, which comprises a therapeutically effective amount of R(+)-N-propargyl-1-aminoindan or a pharmaceutically acceptable salt thereof and a pharmaceutically acceptable carrier.

The subject invention also provides a use of R(+)-N-propargyl-1-aminoindan or a pharmaceutically acceptable salt thereof in the manufacture of a medicament for the treatment of, or alleviation of symptoms of, Multiple System Atrophy.

The subject invention also provides a product containing R(+)-N-propargyl-1-aminoindan or a pharmaceutically acceptable salt thereof and at least one of levodopa, dopamine agonists, glutamine antagonists, orthostatic hypotension therapeutics, anticholinergics, or drugs to treat male impotence, as a combined preparation for simultaneous, separate or sequential use in treating a Multiple System Atrophy.

The subject invention also provides a product containing R(+)-N-propargyl-1-aminoindan or a pharmaceutically acceptable salt thereof and at least one of levodopa, dopamine agonists, glutamine antagonists, orthostatic hypotension therapeutics, anticholinergics, or drugs to treat male impotence, as a combined preparation for simultaneous, separate or sequential use in alleviating a symptom of Multiple System Atrophy.

The subject invention also provides a use of R(+)-N-propargyl-1-aminoindan or a pharmaceutically acceptable salt thereof for the manufacture of a medicament for use in alleviating a symptom of Multiple System Atrophy in a patient who is already being treated with at least one of levodopa, dopamine agonists, glutamine antagonists, orthostatic hypotension therapeutics, anticholinergics, or drugs to treat male impotence.

DETAILED DESCRIPTION

The subject invention provides a method of treating a subject suffering from Multiple System Atrophy, comprising administering to the subject an amount of R(+)-N-propargyl-1-aminoindan or a pharmaceutically acceptably salt thereof effective to treat the subject.

The subject invention also provides a method of alleviating a symptom of Multiple System Atrophy in a subject afflicted with Multiple System Atrophy, comprising administering to the subject an amount of R(+)-N-propargyl-1-aminoindan or a pharmaceutically acceptable salt thereof effective to alleviate the symptom of Multiple System Atrophy in the subject.

In an embodiment of the method, the symptoms of Multiple System Atrophy is tremor, muscular rigidity, hypokinesia, impaired balance, impaired speech, impaired swallowing, ataxia, orthostatic hypotension, impotence, urinary incontinence or urinary retention.

In another embodiment of the method, the form of multiple system atrophy is a striatonigral degeneration form, a Shy-Drager syndrome form, or a sporadic olivopontocerebellar atrophy form.

In yet another embodiment of the method, the amount of R(+)-N-propargyl-1-aminoindan or of the pharmaceutically acceptable salt thereof is from 0.01 mg to 20 mg per day.

In yet another embodiment of the method, the amount of R(+)-N-propargyl-1-aminoindan or of the pharmaceutically acceptable salt thereof is from 0.5 mg to 5 mg per day.

In yet another embodiment of the method, the amount of R(+)-N-propargyl-1-aminoindan or of the pharmaceutically acceptable salt thereof is 2 mg per day.

In yet another embodiment of the method, the amount of R(+)-N-propargyl-1-aminoindan or of the pharmaceutically acceptable salt thereof is 1 mg per day.

In yet another embodiment of the method, the administration is of the pharmaceutically acceptable salt of R(+)-N-propargyl-1-aminoindan.

In yet another embodiment of the method, the pharmaceutically acceptable salt is esylate, mesylate, sulfate or tartrate.

In yet another embodiment of the method, the pharmaceutically acceptable salt is mesylate.

In yet another embodiment of the method, the amount of R(+)-N-propargyl-1-aminoindan mesylate is 1.56 mg per day.

In yet another embodiment of the method, the administration is oral, parenteral, rectal or transdermal administration.

In yet another embodiment, the method further comprises administration of adjunctive therapy including, but not limited to, levodopa, dopamine agonists, glutamine antagonists, orthostatic hypotension therapeutics, anticholinergics, or drugs to treat male impotence.

In a further embodiment of the method, the subject at the time of first administration of R(+)-N-propargyl-1-aminoindan mesylate or a pharmaceutically acceptable salt thereof has been receiving an adjunctive therapy including, but not limited to, levodopa, dopamine agonists, glutamine antagonists, orthostatic hypotension therapeutics, anticholinergics, or drugs to treat male impotence for the alleviation of a symptom of Multiple System Atrophy.

In yet a further embodiment of the method, the R(+)-N-propargyl-1-aminoindan or the pharmaceutically acceptable salt thereof is in a pharmaceutical composition.

The subject invention also provides a pharmaceutical composition comprising in unit dosage form R(+)-N-propargyl-1-aminoindan or a pharmaceutically acceptable salt thereof and at least one of dopamine agonists, glutamine antagonists, orthostatic hypotension therapeutics, anticholinergics, or drugs to treat male impotence.

The subject invention also provides a pharmaceutical composition for use in the treatment of, or alleviation of symptoms of, Multiple System Atrophy, Which comprises a therapeutically effective amount of R(+)-N-propargyl-1-aminoindan or a pharmaceutically acceptable salt thereof and a pharmaceutically acceptable carrier.

The subject invention also provides a use of R(+)-N-propargyl-1-aminoindan or a pharmaceutically acceptable salt thereof in the manufacture of a medicament for the treatment of, or alleviation of symptoms of, Multiple System Atrophy.

The subject invention also provides a product containing R(+)-N-propargyl-1-aminoindan or a pharmaceutically acceptable salt thereof and at least one of levodopa, dopamine agonists, glutamine antagonists, orthostatic hypotension therapeutics, anticholinergics, or drugs to treat male impotence, as a combined preparation for simultaneous, separate or sequential use in treating a Multiple System Atrophy.

The subject invention also provides a product containing R(+)-N-propargyl-1-aminoindan or a pharmaceutically acceptable salt thereof and at least one of levodopa, dopamine agonists, glutamine antagonists, orthostatic hypotension therapeutics, anticholinergics, or drugs to treat male impotence, as a combined preparation for simultaneous, separate or sequential use in alleviating a symptom of Multiple System Atrophy.

The subject invention also provides a use of R(+)-N-propargyl-1-aminoindan or a pharmaceutically acceptable salt thereof for the manufacture of a medicament for use in alleviating a symptom of Multiple System Atrophy in a patient who is already being treated with at least one of levodopa, dopamine agonists, glutamine antagonists, orthostatic hypotension therapeutics, anticholinergics, or drugs to treat male impotence.

The present invention thus provides the R-(+)-enantiomer of N-propargyl-1-aminoindan ("R(+)PAI") of the formula (I):

and pharmaceutically acceptable acid additions salts thereof for the treatment of human patients for Multiple System Atrophy. The present invention also provides pharmaceutical compositions comprising the compound R(+)PAI, their preparations and methods of treatment of Multiple System Atrophy with the pharmaceutical compositions.

Rasagiline is the INN (International Nonproprietary Name) and USAN (United States Adopted Name) of the chemical substance R-(+)-N-propargyl-1-aminoindan.

R(+)PAI may be obtained by optical resolution of racemic mixtures of R and S-enantiomer of N-propargyl-1-aminoindan (PAI). Such a resolution can be accomplished by any conventional resolution method, well known to a person skilled in the art, such as those described in "Enantiomers, Racemates and Resolutions" by J. Jacques, A. Collet and S. Wilen, Pub. John Wiley & Sons, N.Y., 1981. For example, the resolution may be carried out by preparative chromatography on a chiral column. Another example of a suitable resolution method is the formation of diastereomeric salts with a chiral acid such as tartaric, malic, mandelic acid or N-acetyl derivatives of amino acids, such as N-acetyl leucine, followed by recrystallisation to isolate the diastereomeric salt of the desired R enantiomer.

The racemic mixture of R and S enantiomers of PAI may be prepared, e.g. as described in WO95/11016. The racemic mixture of RAI can, also be prepared by reacting 1-chloroindan or 1-bromoindan with propargylamine. Alternatively, this racemate may be prepared by reacting propargylamine with 1-indanone to form the corresponding imine, followed by reduction of the carbon-nitrogen double bond of the imine with a suitable agent, such as sodium borohydride.

In accordance with this invention, R(+)PAI can also be prepared directly from the optically active R-enantiomer of 1-aminoindan by reaction with propargyl bromide or propargyl chloride in the presence of an organic or inorganic base and optionally in the presence of a suitable solvent. A preferred method of preparation of the aforementioned compound is the reaction between R-1-aminoindan with propargyl chloride using potassium bicarbonate as a base and acetonitrile as solvent.

The compound R(+)PAI may be prepared as pharmaceutical compositions particularly useful for the treatment of Multiple System Atrophy. Such compositions may comprise the compound of R(+)PAI or pharmaceutically acceptable acid addition salts thereof, together with pharmaceutically acceptable carriers and/or excipients. In the practice of this invention, pharmaceutically acceptable salts include, but are not limited to, the mesylate, maleate, fumarate, tartrate, hydrochloride, hydrobromide, esylate, p-tolunesulfonate, benzoate, acetate, phosphate and sulfate salts.

The compositions may be prepared as medicaments to be administered orally, parenterally, rectally or transdermally. Suitable forms for oral administration include tablets, compressed or coated pills, dragees, sachets, hard or soft gelatin capsules, sublingual tablets, syrups and suspensions; for parenteral administration the invention provides ampoules or vials that include an aqueous or non-aqueous solution or emulsion; for rectal administration there are provided suppositories with hydrophilic or hydrophobic vehicles; and for topical application as ointments and transdermal delivery there are provided suitable delivery systems as known in the art.

Specific examples of pharmaceutical acceptable carriers and excipients that may be used to formulate oral dosage forms of the present invention are described, e.g., in U.S. Pat. No. 6,126,968 to Peskin et al., issued Oct. 3, 2000. Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); *Advances in Pharmaceutical Sciences Vol* 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.).

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, dicalcium phosphate, calcium sulfate, mannitol, sorbitol, microcrystalline cellulose and the like. Suitable binders include starch, gelatin, natural sugars such as glucose or beta-lactose, corn starch, natural and synthetic gums such as acacia, tragacanth, or sodium alginate, povidone, carboxymethylcellulose, polyethylene glycol, waxes, and the like. Lubricants used in these dosage forms include sodium oleate, sodium stearate, sodium benzoate, sodium acetate, sodium chloride, stearic acid, sodium stearyl fumarate, talc and the like. Disintegrators include, without limitation, starch, methyl cellulose, agar, bentonite, xanthan gum, croscarmellose sodium, sodium starch glycolate and the like.

Rasagiline mesylate in a 1 mg tablet is commercially available for use in Parkinson's disease treatment as Azilect® from Teva Pharmaceutical Industries, Ltd. (Petach Tikva, Israel) and H. Lundbeck A/S (Copenhagen, Denmark). The cognitive and behavioral adverse events of hallucinations, confusion, depression, somnolence and other sleep disorders in subjects treated with Azilect® are few and do not exceed the incidence seen in subjects receiving placebo by more than 3 percent. (Parkinson Study Group, Tyramine Challenge to Assess the Safety of Rasagiline Monotherapy in a Placebo-Controlled Multicenter Trial for Early Parkinson's Disease (The TEMPO Study), Neurology, 2001, 56:A345) The most commonly reported adverse events in rasagiline-treated subjects are pain, headache and dizziness. Side effects typically associated with other dopaminergic medications, such as hallucinations, somnolence, edema, nausea, vomiting, and diarrhea, are infrequently reported in rasagiline-treated subjects. (Stern et al., Double-Blind, Randomized, Controlled Trial of Rasagiline as Monotherapy in Early Parkinson's Disease Patients, *Mov. Disord.,* 2004, 19(8):916-923)

R(+)PAI compositions may be used alone to treat Multiple System Atrophy, or alternatively, they may be used as an adjunct to existing Multiple System Atrophy treatments. R(+)PAI may be administered at different times and separate from other Multiple System Atrophy treatments, or as a combined pharmaceutical composition of R(+)PAI with at least one Multiple System'Atrophy treatment. Such treatment may be, for example, treatment with Levodopa, dopamine agonists such as bromocriptine, lisuride and apomorphine and glutamine antagonists such as amantadine, DDAVP or anticholinergics such as oxybutinin shown to help with the various urinary symptoms of MSA, orthostatic hypotension therapies such as ephedrine, fludrocortisone and midodrine or other drugs that raise blood pressure, or penile implants or drugs to treat male impotence. Thus, for example, a pharmaceutical composition for oral use in the form of tablets or capsules may comprise R(+)-N-propargyl-1-aminoindan, Levodopa, and a decarboxylase inhibitor. Such a composition may comprise 0.01-20 mg of R(+)-N-propargyl-1-aminoindan, 50-100 mg of Levodopa, and 12.5-50 mg of benserazide.

The preferred dosages of R(+)PAI in any of the disclosed compositions may be within the following ranges: for oral or suppository formulations 0.01-20 mg per dosage unit to be taken daily, preferably 0.5-5 mg per dosage unit to be taken daily and more preferably 1 mg or 2 mg per dosage unit to be taken daily may be used; and for injectable formulations 0.05-10 mg/ml per dosage unit to be taken daily and more preferably 0.5-3 mg/ml per dosage unit to be taken daily and more preferably 1 mg/ml per dosage unit to be taken daily may be used.

By 0.01-20 mg it is meant that all hundredth, tenth and integer unit amounts within the range are specifically disclosed as part of the invention. Thus, 0.02, 0.03 . . . 0.09; 0.1, 0.2 . . . 0.9; and 1, 2 . . . 19 mg unit amounts are included as embodiments of this invention.

As used herein, "parkinsonian" and "parkinsonism" refer to symptoms of the striatonigral degeneration form of MSA, which symptoms resemble those of Parkinson's disease, but whose clinicopathology is separate and distinct from Parkinson's disease.

EXPERIMENTAL DETAILS

Example 1

| | |
|---|---:|
| R(+)-N-propargyl-1-aminoindan mesylate | 3.12 mg/tablet |
| Mannitol | 62.5 mg/tablet |
| Maltodextrin (Maltrin 150) | 36.0 mg/tablet |
| Croscarmellose sodium (Ac-Di-Sol) | 2.1 mg/tablet |
| Talc | 1.5 mg/tablet |

Example 2

| | |
|---|---:|
| R(+)-N-propargyl-1-aminoindan mesylate | 1.56 mg/tablet |
| Mannitol | 79.14 mg/tablet |
| Starch | 10.0 mg/tablet |
| Pregelatinized starch | 10.0 mg/tablet |
| Colloidal silicon dioxide | 0.6 mg/tablet |
| Talc | 2.0 mg/tablet |
| Stearic acid | 2.0 mg/tablet |

Example 3

| | |
|---|---:|
| R(+)-N-propargyl-1-aminoindan mesylate | 3.12 mg/tablet |
| Mannitol | 76.58 mg/tablet |
| Starch | 10.0 mg/tablet |
| Pregelatinized starch | 10.0 mg/tablet |
| Colloidal silicon dioxide | 0.6 mg/tablet |
| Citric acid | 1.0 mg/tablet |
| Talc | 2.0 mg/tablet |

Example 4

| | |
|---|---:|
| R(+)-N-propargyl-1-aminoindan mesylate | 3.12 mg/tablet |
| Mannitol | 69.88 mg/tablet |
| Lactose (hydrous) | 14.0 mg/tablet |
| Starch | 14.0 mg/tablet |
| Glyceryl Behenate (Compitrol 888 ATO) | 2.0 mg/tablet |

Example 5

| | |
|---|---:|
| R(+)-N-propargyl-1-aminoindan mesylate | 3.12 mg/tablet |
| Mannitol | 77.28 mg/tablet |
| Starch | 10.0 mg/tablet |
| Starch STA-RX 1500 | 10.0 mg/tablet |
| Colloidal silicon dioxide, Aerosil | 0.6 mg/tablet |
| Hydrogenated vegetable type I (Sterotex Dritex) | 2.0 mg/tablet |

(1.56 mg of R(+)-N-propargyl-1-aminoindan mesylate amounts to 1.0 mg of the base compound R(+)-N-propargyl-1-aminoindan)

Example 6

Mouse Model of MSA

A suitable model for MSA is described by Stefanova et al. (Am. J. Pathol. March 2005, 166(3):869-76; Trends Neurosci. 2005, 28(9):501-6). This model acts by inducing oxidative stress in transgenic mice with oligodendroglial α-synuclein expression. The model has been shown to reproduce the cardinal neuropathological features of MSA including striatonigral degeneration (SND), olivopontocerebellar atrophy (OPCA), astrogliosis and microgliosis combined with oligodendroglial insoluble α-synuclein inclusions. The selective neuronal cell death pattern typical of MSA is achieved by combining mitochondrial inhibition by 3-nitropropionic acid (3-NP).

A total of 36 (PLP) α-synuclein transgenic mice over 6 months of age were used. The mice were randomized into four groups as shown in Table 1.

TABLE 1

| Group | N | 3-NP intoxication | Rasagiline (mg/kg b.w.) | Mortality N (%) |
|---|---|---|---|---|
| "healthy" controls | 6 | – | — | 0 (0) |
| MSA | 10 | + | 0 | 2 (20) |
| MSA + Low dose Rasagiline | 10 | + | 0.8 | 2 (20) |
| MSA + High dose Rasagiline | 10 | + | 2.5 | 1 (10) |

Chronic intoxication with 3-NP was done according to a previously used paradigm pathology (i.e. 4×10 mg/kg, 4×20 mg/kg, 4×40 mg/kg, 4×50 mg/kg intraperitoneal injections every $12^{th}$ hour for a period of two weeks) to model MSA pathology.

The mice were further divided into groups as follows: Control group (saline tested, n=10), low dose rasagiline group (0.6 mg/kg; n=10) and high dose rasagiline group (2 mg/kg; n=10). Rasagiline was delivered subcutaneously every 24 hours starting 24 hours one week before the intoxication with 3-NP and lasting for an additional week, i.e., for a total period of 4 weeks.

Activity and Toxicity of Rasagiline: Analysis of MAO-A and MAO-B Activity

Efficacy of Rasagiline treatment was determined by biochemical measurement of the inhibition of MAO-A and MAO-B activity in the different treatment groups. Two mice per group were sacrificed under deep thiopental anesthesia by cervical translocation. Brains were immediately removed and snap-frozen in liquid nitrogen and further stored at −80° C. Tissue homogenates were preincubated with clorgyline or deprenyl in order to inhibit MAO-A or MAO-B respectively. Incubation was carried on with 14C-labeled PEA (10 μM) for MAO-B determination and 14C-HT (100 μM) for MAO-A determination. Reaction was stopped by acidification and labeled metabolites were extracted into toluene/ethyl acetate and counted by beta-counter.

General observation and daily body weight measurement did not indicate any toxic effects of Rasagiline. The biochemical activity of MAO-A and MAO-B in the different treatment groups was determined at the end of the experiment. Rasagiline treatment in both concentrations induced significant inhibition of MAO activity. The results are shown in Table 2.

TABLE 2

| Group | Treatment | MAO-A activity (mean dpm ± SD) | MAO-B activity (mean dpm ± SD) |
|---|---|---|---|
| control | saline | 4179.75 ± 200 | 8644.40 ± 1409 |
| MSA | saline | 5126.58 ± 307 | 12783.8 ± 580 |
| MSA | Rasagiline 0.8 mg/kg | 1463.10 ± 219 | 370.01 ± 321 |
| MSA | Rasagiline 2.5 mg/kg | 724.06 ± 65 | 80.94 ± 14 |

Motor Behavior and General Motor Score

Behavioral tests were performed blindly to the treatment status according to the following procedures and described in Fernagut et al.: clinical scale, stride length, spontaneous locomotor activity. (Neuroscience, 2002; 114(4):1005-17) The general observations (clinical scale) were performed daily during the entire experimental period and the remainder of the tests are performed during the last three days prior to sacrificing the mice.

Motor behavior was evaluated daily by a general clinical score and with additional motor behavioral tests (Flex Field, pole test and stride length) according to previously described protocols (Stefanova et al., Oxidative stress in transgenic mice with oligodendroglial alpha-synuclein overexpression replicates the characteristic neuropathology of multiple system atrophy, *Am. J. Pathol.* 2005; 166:869-76) during the third week (days 16-19) and fourth week (days 25-28) of the experiment.

Figure 1:
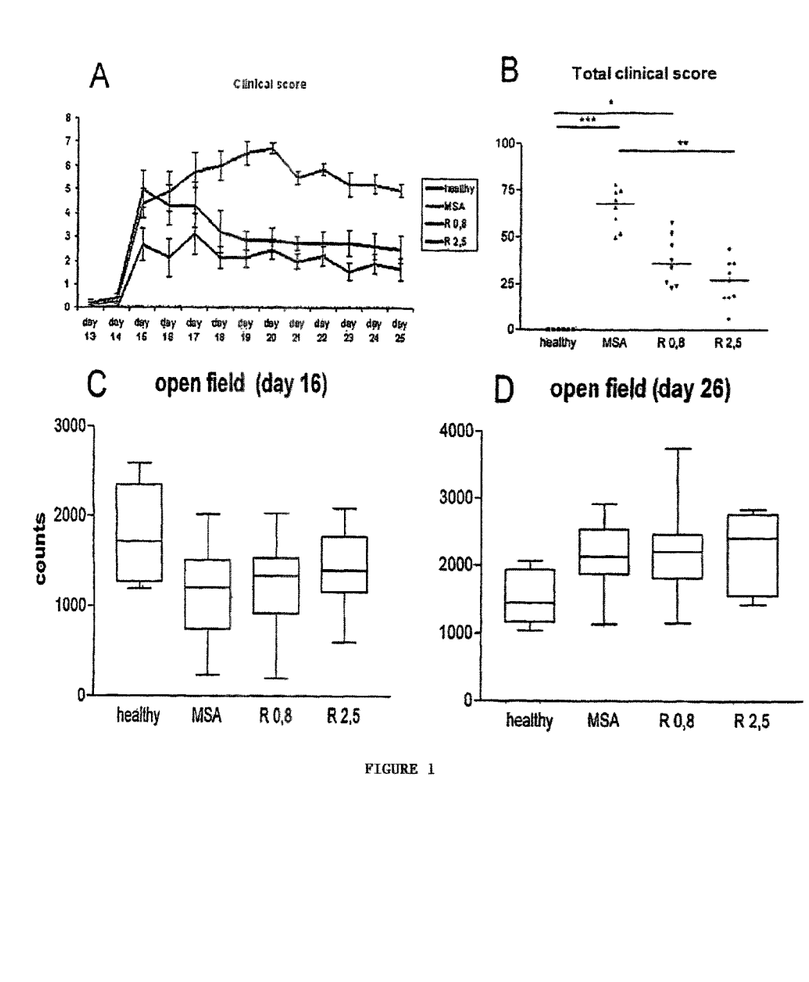
FIG. 1 Behavioral tests. The clinical score evaluation (A and B) was performed during the whole experimental period and is presented as daily mean values per group (A) or as sum per mouse per group for the total observation period (B). Open field activity, rearing, pole test (T-turn and T-total) and stride length test were performed during the second (C, E, G, I, and K) and third (D, F, H, J, and L) week after the beginning of 3NP intoxication. Significant group differences at * $p<0.001$;  $p<0.01$: and * $p<0.05$.

The groups were evaluated daily during the whole experimental period with a general motor score according to a previously published rating scale. First signs of motor disturbance were observed on day 13 of the experiment (day 6 after 3-NP intoxication) and progressed further in the MSA groups compared to the non-intoxicated controls (FIGS. 1A and 1B). Treatment with rasagiline induced significant improvement of general motor impairment (FIG. 18). In sum, rasagiline improved several important aspects of impaired motor behavior in the transgenic MSA mouse model.

Standardized Motor Behavioral Scale for Assessment of the Severity of 3-NP-induced Motor Disability in Mice A previously described rating scale (Fernagut et al., Subacute systemic 3-nitropropionic acid intoxication induces a distinct motor disorder in adult C57B1/6 mice: Behavioural and histopathological characterization, *Neuroscience* 2002; 114:1005-17) was used for evaluation of hindlimb clasping, general locomotor activity, hindlimb dystonia, truncal dystonia and postural challenge response (0, normal; 1 slightly disturbed, and 2 markedly disabled). The rating was performed every 24 h starting after the first 3-NP intoxication (day 7) and lasting until the end of the experiment. A total daily score per animal for each session was determined as well as a total sum score per animal per group for the whole testing period.

Pole Test

The pole test (Id.; and Matsuura et al., Pole test is a useful method for evaluating the mouse movement disorder caused by striatal dopamine depletion, *Journal of Neuroscience Methods* 1997; 73:45-8) was performed on day 17 and day 25 of the experiment. Each mouse was habituated to the test the day before. A wooden vertical pole with rough surface, 1 cm wide and 50 cm high was applied. The mouse was placed with the head up at the top of the pole and the time for turning downwards ($T_{turn}$) as well as the total time for climbing down the pole until the mouse reached the floor with the four paws ($T_{total}$) was taken in 5 trials. The best performance of all the five trials was kept for the statistical analysis (Fernagut et al., In vivo models of multiple system atrophy, *Mov Disord.* 2005; 20 Suppl 12:S57-S63). If a mouse was unable to perform the test, a default value of 120 s was taken into account.

Significant disability to perform the test was observed in 3-NP treated animals on days 17 and 25 as registered by elongation of t-turn and T-total (FIGS. 1G and 1I). Rasagiline significantly reduced prolonged movement times (T-turn and T-total) during the fourth week (day 25).

Open Field and Rearing Activity

To test the locomotor activity of the mice we applied the Flex Field Activity System, (San Diego Instruments, San Diego, Calif.) which allows monitoring and real-time counting of horizontal and vertical locomotor activity by 544 photo-beam channels. Mice were placed in the center of the open field (40.5×40.5×36.5 cm) and tested for a 15 min period always at the same time of the day (5.00 p.m.). The tests were performed in a dark room that was completely isolated from external noises and light during the test period. The sum of counts in the horizontal and vertical plane at day 16 and on day 26 of the experiment was further analyzed.

Flex Field Activity

3-NP intoxication induced a transient decrease of open field and rearing activity on day 16 (FIG. 1E). Significant effects of the rasagiline treatment were observed neither upon open field activity nor on rearing behavior at any of the time points studied (FIGS. 1C-1F).

Stride Length

The stride length of the hindlimbs of the mice was measured at baseline and before sacrificing them after a habituation to the test for 3 days before its performance. The limbs of each animal were wetted with a non-toxic food color and the mouse was let to run on a strip of paper (42 cm long, 4.5 cm wide) down a bright corridor towards a dark goal box. After four runs, the stride length of the forelimbs and the hindlimbs on each side was measured, excluding the beginning (7 cm) and the end (7 cm) of the run. The mean stride length for was determined.

Stride length test was performed on day 18-19 and day 27-28 after first 3-NP intoxication. Stride length was shortened at both time points as a result of 3-NP intoxication (FIGS. 1K and 1L). Rasagiline reversed shortened stride length on day 18-19 and reversed stride length impairment on day 27-28.

Neuropathology

Neuropathological examination of the brains was performed after transcardial perfusion of 4% paraformaldehyde (PFA) under deep thiopental anesthesia. Brains were quickly removed, postfixed in the same fixative for 1 hour at 4° C., and then kept in 25% sucrose solution until they sunk. The brains were slowly frozen in with 2-methylbutan and kept at −80° C. until processing. Serial sections throughout the whole brain were cut on a freezing microtome (Leica, Nussloch, Germany).

Sections underwent the following immunohistochemical stainings: tyrosinehydroxylase antibody (Sigma) used to visualize dopaminergic neurons in SNc, dopamine and cyclic adenosine 3',5'-monophosphate-regulated phosphoprotein 32 (DARPP-32)(New York Hospital-Cornell Medical Centre) used to visualize medium sized spiny neurons in striatum and Purkinje cells in cerebellar cortex, Glial Fibrillary Acidic Protein (GFAP)(Roche Diagnostics GmBH) used to visualize astroglial reaction, CD11b (Serotec) used to visualize microglial reaction and Bcl-2, Bcl-X1 and Bax apoptic/anti-apoptotic markers. One full series was stained with cresyl violet.

The following antibodies were used in this study: monoclonal anti-DARPP-32 (1:2000), monoclonal anti-TH (Sigma, St. Louis, Mo., 1:500), monoclonal anti-GFAP (Roche, Vienna, Austria 1:100), monoclonal anti-CD11b (Serotec, Oxford, UK, 1:100), polyclonal anti-activated capase 3 (Transduction Laboratories, Lexington, Ky., 1:200), monoclonal anti-Bax (Santa Cruz Biotechnology, 1:100), monoclonal anti-Bc12 (Santa Cruz Biotechnology, 1:100), and monoclonal anti-BclX (Chemicon, Temecula, Calif., 1:100). Secondary antibodies were biotinylated horse anti-mouse IgG, goat anti-rat IgG, or goat anti-rabbit IgG (Vector, Burlingame, Calif.). Immunohistochemical reaction was developed with 3,3'-diaminobenzidine.

All morphometric analyses were done blinded to the treatment of the animal's observer. Stereology was applied using a computer-assisted image analysis system (Nikon E-800 microscope, Nikon digital camera DXM 1200; Stereo Investigator Software, MicroBrightField Europe e.K., Magdeburg, Germany). Stereological methods (Mayhew et al., If you assume, you can make an as out of u and me': a decade of the disector for stereological counting of particles in 3D space. *J. Anat.*, 1996; 188 (Pt 1):1-15) were used to count number of striatal neurons, number of dopaminergic neurons in the substantia nigra pars compacta, pontine nuclei, and inferior olive. Purkinje cells in the cerebellum and glial reaction throughout the entire brain are analyzed to the Paxinos and Franklin mouse brain atlas (1997, Academic Press, San Diego). Purkinje cells were counted in a region outlined to include only the Purkinje cell layer (German et al., Degeneration of neurons and glia in the Niemann-Pick C mouse is unrelated to the low-density lipoprotein receptor. *Neuroscience*, 2001; 105:999-1005).

All data are expressed as mean values±SEM. For all statistical tests performed, a probability level of 5% (p<0.05) is considered significant.

Statistical comparison between the groups was performed using either parametric or non-parametric ANOVA (one-way analysis of variance), followed by post-hoc Tukey's or Kurskal-Wallis test. Correlations between histopathology and behavioral variables are obtained by using linear regressions. Survival is assessed within groups by Kaplan-Meier survival curves and morphological parameters of different groups are compared using ANOVA.

Striatonigral Degeneration

Figure 2:
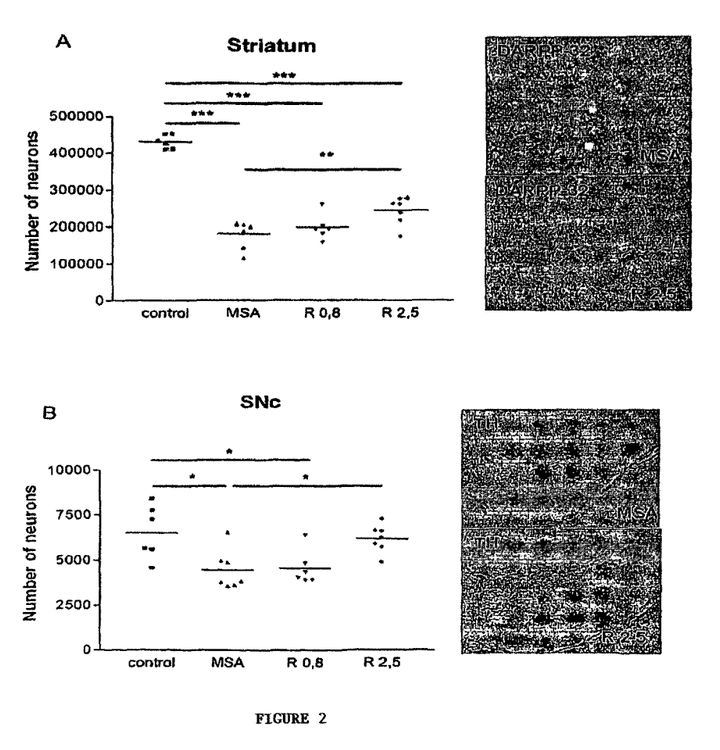
FIG. 2 Striatonigral degeneration. Neuronal numbers in striatum (A) and substantia nigra pars compacta (B) in control mice, MSA mice, and MSA mice treated with rasagiline 0.8 mg/kg (R 0.8) or 2.5 mg/kg (R 2.5). Photomicrographs demonstrate DARPP32-immunohistochemistry in striatum and TH-immunohistochemistry in SNc of a MSA mouse and a rasagiline (2.5 mg/kg) treated MSA mouse. Significant group differences at * $p<0.001$;  $p<0.01$: and * $p<0.05$.

3-NP intoxication of the (PLP)-α-synuclein mice induced loss of striatal DARPP-32-immunoreactive medium spiny neurons. This neuronal loss was partially prevented by rasagiline treatment, however, numbers of neurons did not reach levels of non-intoxicated controls (FIG. 2A). Similarly, intoxication with 3-NP induced loss of TH-immunopositive neurons in SNc, but rasagiline treatment completely protected nigral neurons against the intoxication (FIG. 2B).

Olivopontocerebellar Atrophy

Figure 3:
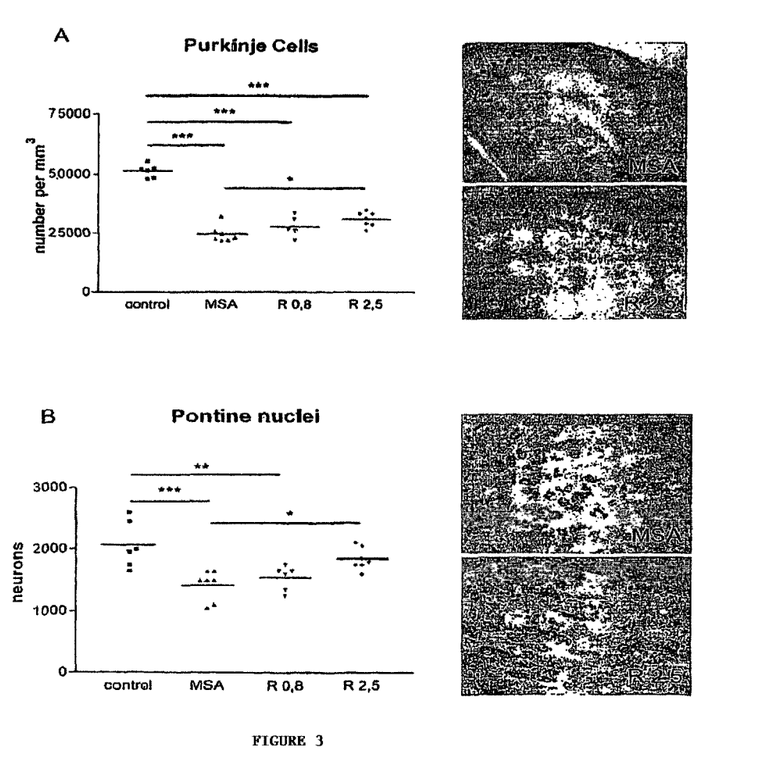
FIG. 3 Olivopontocerebellar atrophy. Morphometric results in the cerebellar cortex (Purkinje cells) (A), pontine nuclei (B) and inferior olive (C) of control mice, MSA mice, and MSA mice treated with rasagiline 0.8 mg/kg (R 0.8) or 2.5 mg/kg (R 2.5). Photomicrographs demonstrate DARPP32-immunohistochemistry of the cerebellar cortex (Purkinje cells), and cresyl-violet staining of pontine nuclei and inferior olives of a MSA mouse and a rasagiline (2.5 mg/kg) treated MSA mouse. Significant group differences at * $p<0.001$;  $p<0.01$.

3-NP intoxication induced loss of neurons in the cerebellum (Purkinje cells), pons (pontine nuclei) and inferior olives. Treatment with rasagiline had neuroprotective effects in the olivopontocerebellar system similar to that observed in the striatonigral system. Daily treatment with 2.5 mg/kg rasagiline for 4 weeks induced partial protection of Purkinje cells (FIG. 3A) and neurons of the inferior olives (FIG. 3C) without reaching neuronal numbers of healthy controls. Pontine nuclei were completely protected by rasagiline treatment against 3-NP intoxication (FIG. 3 B).

Additional immunohistochemistry for GFAP and CD11b to determine effects of rasagiline treatment on astroglial and microglial activation were performed. No differences were observed in the staining pattern of treated and untreated mice. Further, immunohistochemistry for bcl-2, bcl-X, and bax was performed, yet no conclusive results could be obtained with this method regarding the mechanisms of cell death and rasagiline neuroprotection involved in the model.

The neuropathological results indicate that rasagiline treatment has protective effect in a transgenic mouse model of MSA with diminishing the loss of neurons in striatum, SNc, cerebellum, pons and inferior olives. This pathological finding correlates with improved motor behavior scores of the rasagiline treatment group.

What is claimed is:

1. A method of treating a subject suffering from Multiple System Atrophy, consisting of administering to the subject an amount of R(+)-N-propargyl-1-aminoindan or a pharmaceutically acceptably salt thereof alone or R(+)-N-propargyl-1-aminoindan in combination with levodopa, dopamine agonists, glutamine antagonists, orthostatic hypotension therapeutics, anticholinergics, or a drug to treat male impotence, effective to treat the subject.

2. A method of alleviating a symptom of Multiple System Atrophy in a subject afflicted with Multiple System Atrophy, consisting of administering to the subject an amount of R(+)-N-propargyl-1-aminoindan or a pharmaceutically acceptable salt thereof effective to alleviate the symptom of Multiple System Atrophy in the subject, wherein the symptom of Multiple System Atrophy is tremor, muscular rigidity, hypokinesia, impaired balance, impaired speech, impaired swallowing, ataxia, orthostatic hypotension, impotence, urinary incontinence or urinary retention.

3. The method of claim 1, wherein the form of multiple system atrophy is a striatonigral degeneration form, a Shy-Drager syndrome form, or a sporadic olivopontocerebellar atrophy form.

4. The method of claim 1, wherein the amount of R(+)-N-propargyl-1-aminoindan is from 0.5 mg to 20 mg per day.

5. The method of claim 4, wherein the amount of R(+)-N-propargyl-1-aminoindan is from 0.5 mg to 5 mg per day.

6. The method of claim 4, wherein the amount of R(+)-N-propargyl-1-aminoindan is 2 mg per day.

7. The method of claim 4, wherein the amount of R(+)-N-propargyl-1-aminoindan is 1 mg per day.

8. The method of claim 1, wherein the administration is of the pharmaceutically acceptable salt of R(+)-N-propargyl-1-aminoindan.

9. The method of claim 8, wherein the pharmaceutically acceptable salt is esylate, mesylate, sulfate or tartrate.

10. The method of claim 9, wherein the pharmaceutically acceptable salt is mesylate.

11. The method of claim 10, wherein the amount of R(+)-N-propargyl-1-aminoindan mesylate is 1.56 mg per day.

12. The method of claim 1, wherein the administration is oral, parenteral, rectal, or transdermal administration.

13. The method of claim 1, wherein the R(+)-N-propargyl-1-aminoindan or the pharmaceutically acceptable salt thereof and a pharmaceutically acceptable carrier is in a pharmaceutical composition.

14. The method of claim 2, wherein the form of multiple system atrophy is a striatonigral degeneration form, a Shy-Drager syndrome form, or a sporadic olivopontocerebellar atrophy form.

15. The method of claim 2, wherein the amount of R(+)-N-propargyl-1-aminoindan is from 0.5 mg to 20 mg per day.

16. The method of claim 15, wherein the amount of R(+)-N-propargyl-1-aminoindan is from 0.5 mg to 5 mg per day.

17. The method of claim 1, consisting of administering to the subject an amount of R(+)-N-propargyl-1-aminoindan or a pharmaceutically acceptably salt thereof alone, effective to treat the subject.

18. The method of claim 1, consisting of administering to the subject an amount of R(+)-N-propargyl-1-aminoindan or a pharmaceutically acceptably salt thereof in combination with levodopa, dopamine agonists, glutamine antagonists, orthostatic hypotension therapeutics, anticholinergics, or a drug to treat male impotence, effective to treat the subject.

* * * * *